US012496233B2

(12) United States Patent
Glaug et al.

(10) Patent No.: US 12,496,233 B2
(45) Date of Patent: Dec. 16, 2025

(54) MULTI-PURPOSE DISPOSABLE UNDERWEAR

(71) Applicant: Drylock Technologies NV, Zele (BE)

(72) Inventors: Frank Glaug, Eau Claire, WI (US); Karl Andersen, River Falls, WI (US); Ricardo Borrero, Eau Claire, WI (US)

(73) Assignee: Drylock Technologies NV, Zele (BE)

( * ) Notice: Subject to any disclaimer, the term of this patent is extended or adjusted under 35 U.S.C. 154(b) by 979 days.

(21) Appl. No.: 17/250,022

(22) PCT Filed: May 8, 2019

(86) PCT No.: PCT/EP2019/061856
§ 371 (c)(1),
(2) Date: Nov. 5, 2020

(87) PCT Pub. No.: WO2019/215249
PCT Pub. Date: Nov. 14, 2019

(65) Prior Publication Data

US 2021/0236345 A1 Aug. 5, 2021

Related U.S. Application Data

(60) Provisional application No. 62/668,339, filed on May 8, 2018.

(30) Foreign Application Priority Data

Jul. 17, 2018 (NL) ...................................... 2021325

(51) Int. Cl.
*A61F 13/15* (2006.01)
*A61F 13/49* (2006.01)

(52) U.S. Cl.
CPC .. *A61F 13/15739* (2013.01); *A61F 13/15723* (2013.01); *A61F 13/15747* (2013.01);
(Continued)

(58) Field of Classification Search
CPC .......... A61F 13/15739; A61F 13/15723; A61F 13/15747; A61F 13/49017; A61F 13/4906;
(Continued)

(56) References Cited

U.S. PATENT DOCUMENTS 6,702,800 B1 * 3/2004 Vukos ............... A61F 13/49012 604/385.24
2001/0014798 A1 * 8/2001 Fernfors ................ A61F 13/62 156/217
(Continued)

FOREIGN PATENT DOCUMENTS

WO WO-0234182 A2 5/2002
WO WO-2009117492 A2 9/2009
(Continued)

OTHER PUBLICATIONS

"International Application Serial No. PCT/EP2019/061856, International Search Report mailed Jun. 27, 2019", (Jun. 27, 2019), 4 pgs.
(Continued)

*Primary Examiner* — Nicholas J. Weiss
*Assistant Examiner* — Gabriella E Burnette
(74) *Attorney, Agent, or Firm* — Schwegman Lundberg & Woessner, P.A.

(57) ABSTRACT

Disposable articles, and, more particularly, a disposable undergarment including a product chassis configured to serve as a basis of a variety of disposable articles, including disposable underwear without an absorbent core, disposable underwear with an absorbent core designed for menstrual use, and disposable underwear or training pant with an absorbent core designed for incontinence use (adult and child). The product chassis is comprised of multiple sections including an elastomeric composite, containing stretch film,
(Continued)

coupled to one another, each section is designed to provide stretch in a desired direction, thereby resulting in improved securement of the undergarment to a wearer for optimizing fit and comfort for the wearer, while reducing the risk of leakage as well as reducing the amount overall material required for producing the undergarment. Furthermore, the inclusion of an elastomeric composite can provide a smooth contoured fit to a wearer, thereby improving appearance and self-confidence for the wearer.

20 Claims, 10 Drawing Sheets

(52) U.S. Cl.
CPC .... *A61F 13/49017* (2013.01); *A61F 13/4906* (2013.01); *A61F 2013/49055* (2013.01)

(58) Field of Classification Search
CPC ...... A61F 2013/49055; A61F 13/15699; A61F 2013/49022; A61F 2013/49052; A61F 13/49012; A61F 13/4902; A61F 13/66; A41B 9/12
See application file for complete search history.

(56) References Cited

U.S. PATENT DOCUMENTS

| | | | | |
|---|---|---|---|---|
| 2005/0054780 A1* | 3/2005 | Zhou | C09J 123/10 525/240 |
| 2006/0144503 A1* | 7/2006 | Carr | A61F 13/15593 156/160 |
| 2009/0198203 A1* | 8/2009 | Lira | A61F 13/551 604/385.03 |
| 2009/0240221 A1* | 9/2009 | Rothenberger | A61F 13/51496 156/60 |
| 2018/0256410 A1* | 9/2018 | Bäck | B29C 65/74 |

FOREIGN PATENT DOCUMENTS

| | | |
|---|---|---|
| WO | WO-2016112328 A1 | 7/2016 |
| WO | WO-2017158185 A1 | 9/2017 |

OTHER PUBLICATIONS

"International Application Serial No. PCT/EP2019/061856, Written Opinion mailed Jun. 27, 2019", (Jun. 27, 2019), 6 pgs.

* cited by examiner

MULTI-PURPOSE DISPOSABLE UNDERWEAR

PRIORITY APPLICATIONS

This application is a U.S. National Stage Filing under 35 U.S.C. § 371 from International Application No. PCT/EP2019/061856, filed on May 8, 2019, and published as WO2019/215249 on Nov. 14, 2019, which claims the benefit of priority to Netherlands Application No. 2021325, filed on Jul. 17, 2018 and U.S. Application No. 62/668,339, filed on May 8, 2018; the benefit of priority of each of which is hereby claimed herein, and which applications and publication are hereby incorporated herein by reference in their entireties.

FIELD

The present disclosure relates generally to disposable articles, and, more particularly, to a disposable undergarment including a stretchable product chassis configured to serve as a basis for a variety of disposable articles.

BACKGROUND

There are several types of commercially available products for the absorption of bodily fluids. Such absorbent products are available in different types, designs, and dimensions, each one having one or more unique features. For example, training pants, baby diapers, adult diapers, and incontinence guards are products designed for the containment of urine and excrement. There are other types of disposable absorbent articles, such as feminine hygiene products (e.g., heavy and light incontinence pads, pantyliners, etc.) that are designed to contain and absorb urine and/or menses by female wearers. Another type of absorbent article includes underpads configured to absorb and collect body fluid discharge from a person who may be generally confined to a bed or chair, or may otherwise be immobilized.

Current absorbent products in the form of underwear, training pants, or diapers, generally suffer from poor design. For example, in order to hold the product close to the wearer's body so that it does not fall down, elastic strands or other features are usually provided around leg openings and/or waist openings of the absorbent product. However, this type of construction often leads to discomfort to the wearer from the rubbing of the overlapping components and/or seams holding the components together. Additionally, the elastic elements around the leg and waist openings used to hold the garment against the wearer often contribute to leakage. The leakage is due to the gapping between the article and the wearer's body caused by the elastic gatherings, the gapping providing an inconsistent seal. Furthermore, many current absorbent underwear products contribute to a bulky appearance when worn.

Accordingly, improperly-fit absorbent garments can lead to a number of different issues for the wearer of the garment. For example, an improperly-fit garment can be uncomfortable, can adversely affect the wearer's mobility (actual or perceived), and there can be an increased chance of leakage. This in undesirable to a wearer and can be cause for embarrassment and shame. Thus, there exists a need to minimize leakage at the openings and providing a smooth contoured fit to the body of the wearer.

SUMMARY

The present disclosure relates generally to disposable article. More specifically, the present disclosures relates to a disposable undergarment that includes a stretchable product chassis configured to serve as a basis for a variety of disposable articles, including, but not limited to, disposable underwear without an absorbent core, disposable underwear with an absorbent core designed for menstrual use, and disposable underwear or training pant with an absorbent core designed for incontinence use (adult and child). The product chassis is comprised of multiple sections coupled to one another. For example, in one embodiment, a product chassis may generally include three main sections, which includes a front section, a rear section, and a crotch section. Each section of the product chassis generally includes at least two substrate layers containing an elastomeric material disposed there between. In some embodiments, an absorbent core may be disposed between the one or two substrate layers. However, in other embodiments, an absorbent core can be applied on top of the two substrate layers.

The inclusion of an elastomeric material, such as a stretch adhesive, in the construction of the sections of the product chassis results in improved securement of the article to a wearer for reducing the risk of leakage and further improving comfort for the wearer. In particular, each section may be designed to stretch in a desired direction, thereby resulting in improved securement of the undergarment to a wearer for optimizing fit and comfort for the wearer, while reducing the risk of leakage as well as reducing the amount overall material required for producing the undergarment. Furthermore, the inclusion of an elastomeric material can provide a smooth contoured fit to a wearer, thereby improving appearance and self-confidence for the wearer.

In one embodiment, the elastomeric material is a stretch film that can be unwound in the machine direction (MD) along an absorbent article assembly line. The stretchable film can impart a stretchable characteristic to an assembly, for example, after the film is stretched and bonded between two layers of hydrophobic nonwoven materials (under tension), allowing the nonwoven layers to retract after the product is relaxed (no tension). In an example, a stretchable film can be used in place of elastic strands, wherein the film can be applied to augment an extension or contraction characteristic of another stretchable material such as elastic strands or stretchable adhesive. Generally, the elastomeric material is configured to stretch in the machine direction, which is the direction in which the stretchable film was applied to form the elastomeric composite for the front and rear sections of the product chassis. As for the crotch section of the product chassis, it will be a prefabricated elastomeric composite which will also be applied in the machine direction. This elastomeric composite is designed to stretch in the cross direction and not stretch in the machine direction. It is easier to control materials that do not stretch in the machine direction on a high-speed manufacturing line.

The elastomeric material and the two substrate layers form elastomeric composites for each given section of the product chassis (i.e., the front, rear, and crotch sections). Each of the sections may be strategically constructed so as to stretch in a specific direction to help maximize the fit on the wearer from a minimum to a maximum range, thereby accommodating the varying shapes and sizes from wearer to wearer. For example, in one embodiment, the front section, which is generally designed to be fitted against the front, or anterior portion, of a wearer, and the rear section, which is generally designed to be fitted against the rear, or posterior portion, of the wearer, may both be constructed so as to stretch in a machine direction (MD), while the crotch section, which is designed to be fitted against the crotch region of the wearer, may be constructed so as to stretch in a cross direction (CD).

By providing different stretching characteristics for each given section, the product chassis provides a superior fitting undergarment with improved comfort, as well as reducing the risk of leakage and, in some cases, provides a much more economical disposable underwear design. For example, because the undergarment lies flat against a wearer's body in at least the three main areas (front section, rear section, and crotch section), the undergarment is about to provide a smooth contoured fit to the body, such that any gaps caused by overlapping materials are reduced or eliminated. By reducing or eliminating gaps between the garment and the body, the undergarment of the present disclosure provides improved leak resistance over prior art constructions. Additionally, the elastomeric composite provides consistent pressure and smooth contact against the leg and waist during wear when it is stretched, such that improved performance against leakage is obtained.

The smooth interface of the undergarment with the body provides improved comfort for the wearer and reduces the risk of skin irritation, particularly around the crotch and waist areas of the consumer, which are some of the most sensitive areas of the body. More specifically, the elastomeric composite design of the present disclosure eliminates the need for individual elastic strands (under high tension) and stiff materials (nonwoven & adhesive) along the leg openings, which are commonly found in current disposable underwear designs. In addition, the elastomeric composite design of the present disclosure allows for a wearer to participate in physical activities that may otherwise cause irritation, such as active motion of the wearer during walking or running exercises, which generally increases the rubbing action of material against the skin. The softer material and lower tension elastic provided by the undergarment of the present disclosure reduces the risk of skin irritation long the leg and crotch area of the consumer.

The use of at least three separately constructed sections (i.e., the front, rear, and crotch section, which are then coupled to one another to form the final undergarment product (via ultrasonic bonding or the like) minimizes waste of what could otherwise be an expensive elastomeric material. In particular, less material is necessarily required to be removed during the manufacturing process, as compared to the amount of material required to be removed if the undergarment was made entirely from single sheets of elastomeric composites.

BRIEF DESCRIPTION OF THE DRAWINGS

Features and advantages of the claimed subject matter will be apparent from the following detailed description of embodiments consistent therewith, which description should be considered with reference to the accompanying drawings.

Figure 1:
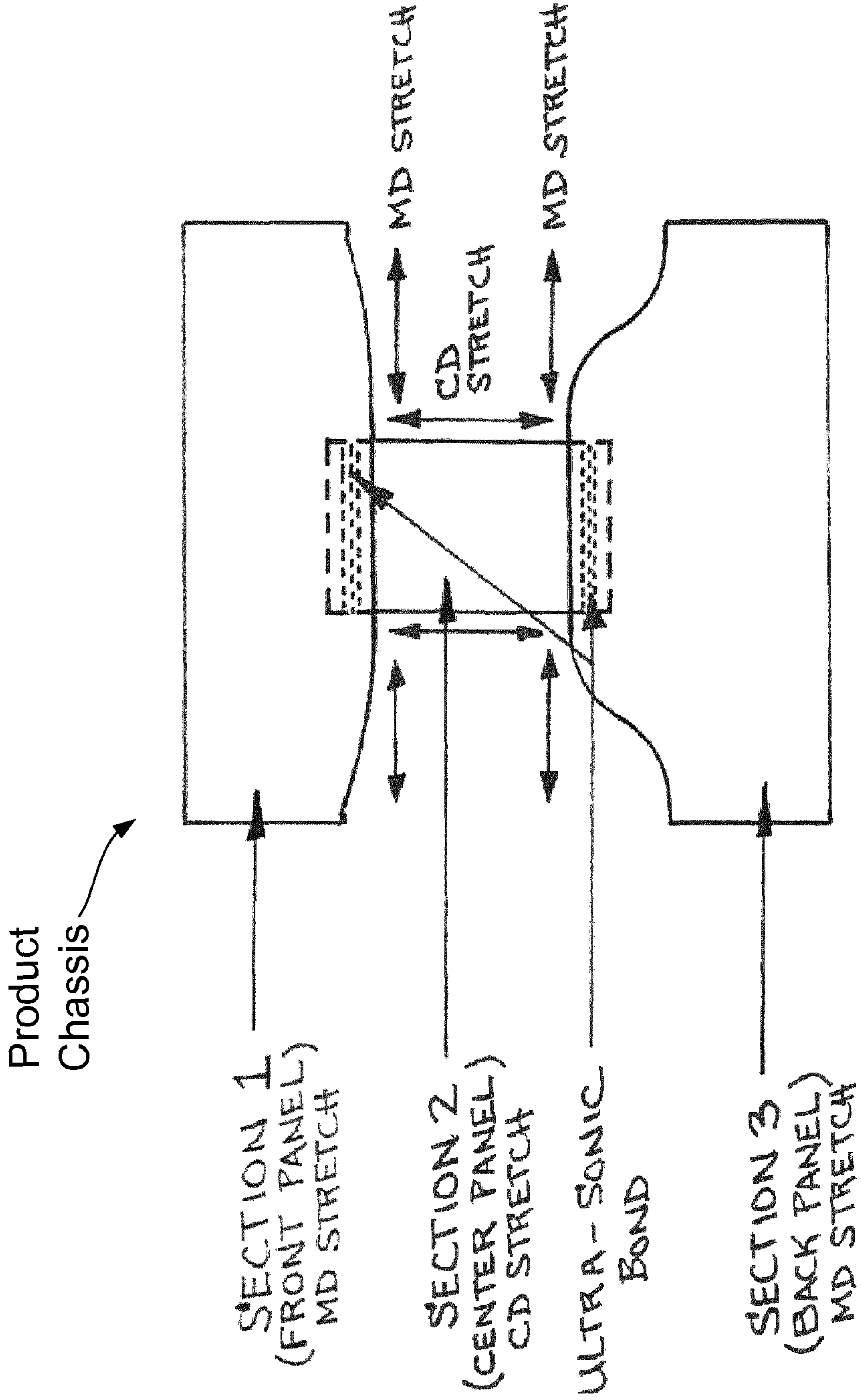
FIG. 1 is a top plan view of one embodiment of disposable underwear consistent with the present disclosure, illustrating the underwear in an unfolded and unsealed state.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The present disclosure relates generally to disposable articles, and, more particularly, to a disposable undergarment including a stretchable product chassis configured to serve as a basis for a variety of disposable articles, including, but not limited to, disposable underwear without an absorbent core, disposable underwear with an absorbent core designed for menstrual use, and disposable underwear or training pant with an absorbent core designed for incontinence use (adult and child). The product chassis is comprised of multiple sections coupled to one another. For example, in one embodiment, a product chassis may generally include three main sections, which includes a front section, a rear section, and a crotch section. Each section of the product chassis generally includes at least two substrate layers containing an elastomeric material disposed there between. In some embodiments, an absorbent core may be disposed between the two substrate layers. However, in other embodiments, an absorbent core can be applied on top of the two substrate layers.

The elastomeric material and the two substrate layers form elastomeric composites for each given section of the product chassis (i.e., the front, rear, and crotch sections). Each of the sections May be strategically constructed so as to stretch in a specific direction to help maximize the fit on the wearer from a minimum to a maximum range, thereby accommodating the varying shapes and sizes from wearer to wearer. For example, in one embodiment, the front section, which is generally designed to be fitted against the front, or anterior portion, of a wearer, and the rear section, which is generally designed to be fitted against the rear, or posterior portion, of the wearer, may both be constructed so as to stretch in a machine direction (MD), while the crotch section, which is designed to be fitted against the crotch region of the wearer, may be constructed so as to stretch in a cross direction (CD).

By providing different stretching characteristics for each given section, the product chassis provides a superior fitting undergarment with improved comfort, as well as reducing the risk of leakage and, in some cases, provides a much more economical disposable underwear design. For example, because the undergarment lies flat against a wearer's body in at least the three main areas (front section, rear section, and crotch section), the undergarment is about to provide a smooth contoured fit to the body, such that any gaps caused by overlapping materials are reduced or eliminated. By reducing or eliminating gaps between the garment and the body, the undergarment of the present disclosure provides improved leak resistance over prior art constructions. Additionally, the elastomeric composite provides consistent pressure and smooth contact against the leg and waist during wear when it is stretched, such that improved performance against leakage is obtained.

The smooth interface of the undergarment with the body provides improved comfort for the wearer and reduces the risk of skin irritation, particularly around the crotch and waist areas of the consumer, which are some of the most sensitive areas of the body. More specifically, the elastomeric composite design of the present disclosure eliminates the need for individual elastic strands (under high tension) and stiff materials (nonwoven & adhesive) along the leg openings, which are commonly found in current disposable underwear designs. In addition, the elastomeric composite design of the present disclosure allows for a wearer to participate in physical activities that may otherwise cause irritation, such as active motion of the wearer during walking or running exercises, which generally increases the rubbing action of material against the skin. The softer material and lower tension elastic provided by the undergarment of the present disclosure reduces the risk of skin irritation long the leg and crotch area of the consumer.

The use of at least three separately constructed sections (i.e., the front, rear, and crotch section, which are then coupled to one another to form the final undergarment product (via ultrasonic bonding or the like) minimizes waste of what could otherwise be an expensive elastomeric material. In particular, less material is necessarily required to be removed during the manufacturing process, as compared to the amount of material required to be removed if the undergarment was made entirely from single sheets of elastomeric composites.

FIG. 1 is a top plan view of one embodiment of disposable underwear consistent with the present disclosure, illustrating the underwear in an unfolded and unsealed state. As shown, the disposable underwear generally includes a stretchable product chassis configured to serve as a basis for a variety of disposable articles, including, but not limited to, disposable underwear without an absorbent core, disposable underwear with an absorbent core designed for menstrual use, and disposable underwear or training pant with an absorbent core designed for incontinence use (adult and child).

The product chassis is comprised of multiple sections coupled to one another. For example, as shown, the product chassis generally includes three main sections: a front section (section 1); a rear section (section 3); and a crotch section (section 2). The front section is generally designed to be fitted against the front, or anterior portion, of a wearer and the rear section is generally designed to be fitted against the rear, or posterior portion, of the wearer, such that front and rear sections generally oppose one another once fitted to the wearer. The crotch section is positioned between the front and rear sections and coupled to each. In some embodiments, the crotch section may include an insert, such as an absorbent core including a liquid-absorbing material (see FIG. 4). However, in other embodiments, including the embodiment currently shown, the product chassis may be devoid of any absorbent core. Rather, an absorbent core can be added after initial construction of the product chassis. For example, commercially available incontinence pads and pantyliners can be attached along the top sheet.

Each of the front section, rear section, and crotch section are stretchable for providing improved securement of the underwear to a wearer for reducing the risk of leakage and further improving comfort for the wearer, as well as a more smooth contoured fit to a wearer, thereby improving appearance and self-confidence for the wearer.

For example, each section of the product chassis generally includes at least two substrate layers containing an elastomeric material disposed there between. In some embodiments, an absorbent core may be disposed between the two substrate layers. However, in other embodiments, an absorbent core can be applied on top of the two substrate layers.

The first substrate may be referred to as a top sheet and is generally configured to contact the wearer's skin and allow fluid from the wearer to flow through it, at least in a direction away from the wearer's skin. In some embodiments, the top sheet may include at least one of a nonwoven material, a hydrophilic or partially hydrophilic material, a nonwoven material with a zone-coated surfactant, and a nonwoven and apertured film. One material that can be used for the top sheet is an SBPP (Spunbond Polypropylene) hydrophilic nonwoven, commercially available from Berry Global, located in Charlotte, NC. The second substrate may be referred to as a back sheet and may generally serve as the outermost layer of the product chassis of the underwear. The back sheet is generally formed from a nonwoven material, to provide a more undergarment-like appearance and feel, and as well as a more cost-effective and comfortable alternative to conventional disposable undergarment designs. The fibers in the nonwoven may include, for example, polypropylene, polyethylene, polyester, bi-component (polypropylene & polyethylene or polyester & polyethylene), cotton, cotton blend, viscose, rayon, etc. or a combination of different fibers. The nonwoven web may include, but is not limited to, Spunbond Polypropylene (SBPP), Spunbond-Meltblown-Spunbond (SMS), Thermal-bonded Carded Web, Spunlace, Laminate, or combinations thereof.

The inclusion of an elastomeric material, which comprises a stretch film bonded between two layers of hydrophobic nonwoven materials, in the construction of the sections of the product chassis results in improved securement of the article to a wearer for reducing the risk of leakage and further improving comfort for the wearer. In particular, each section may be designed to stretch in a desired direction, thereby resulting in improved securement of the undergarment to a wearer for optimizing fit and comfort for the wearer, while reducing the risk of leakage as well as reducing the amount overall material required for producing the undergarment. Furthermore, the inclusion of an elastomeric material can provide a smooth contoured fit to a wearer, thereby improving appearance and self-confidence for the wearer.

In one embodiment, the elastomeric material is a stretch film that is unwound in the machine direction (MD) along an absorbent article assembly line. "Machine direction (MD)", "longitudinal" and the like as used herein are used interchangeably and refer to a direction running parallel to the maximum linear dimension of the structure and includes directions within ±45° of the longitudinal direction.

The stretchable film can impart a stretchable characteristic to an assembly, for example, after the film is stretched and bonded between two layers of hydrophobic nonwoven materials (under tension), allowing the nonwoven layers to retract after the product is relaxed (no tension). In an example, a stretchable film can be used in place of elastic strands and can be applied to augment an extension or contraction characteristic of another stretchable material such as elastic strands or stretchable adhesive. Generally, the elastomeric composite is configured to stretch in the direction in which the stretchable film was applied to form the elastomeric composite. Thus, if the stretchable was applied in a machine direction, then the elastomeric composite will stretch in the machine direction. More specifically, in this embodiment, the elastomeric composite (used for the front and rear sections of the product chassis) will be assembled on the manufacturing machine and stretch in the machine direction. The elastomeric composite used for the crotch (central) sections of the product chassis will be prefabricated, prior to placing on the manufacturing machine. The elastic composite, that will be assembled on the machine, will comprise of three materials. Two of the materials will be a hydrophobic nonwoven, preferably SBPP (Spundbond Polypropylene) or SMS (Spunbond-Meltblown-Spunbond). However, the hydrophobic nonwoven can also be a Through-Air Carded Web or Spunlace. Note that these two nonwoven materials may or may not be similar in basis weights. In addition, they can be different nonwoven types. For example, one may be SBPP and the other SMS. Or one may be SMS and the other Through-Air Carded Web. However, it is desired that the majority of the fibers in the nonwoven material can fuse together during ultrasonic bonding. These nonwoven materials are commercially available from Berry Global located in Charlotte, NC. The last material will be an elastic film, which is commercially available from 3M Corporation located in Minneapolis, MN.

The elastomeric material and the two substrate layers form elastomeric composites for each given section of the product chassis (i.e., the front, rear, and crotch sections). Each of the sections may be strategically constructed so as to stretch in a specific direction to help maximize the fit on the wearer from a minimum to a maximum range, thereby accommodating the varying shapes and sizes from wearer to wearer.

For example, in one embodiment, the front section and the rear section are both constructed so as to stretch in a machine direction (MD), while the crotch section is constructed so as to stretch in a cross direction (CD). "Cross direction (CD)", "lateral" or "transverse" and the like as used herein are used interchangeably and refer to a direction which is orthogonal to the longitudinal direction and includes directions within ±45° of the transversal direction. The product can be folded (e.g., in half) and ultrasonically bonded at the side edges to provide a disposable pull-up undergarment. By providing different stretching characteristics for each given section, the product chassis provides a superior fitting undergarment with improved comfort, as well as reducing the risk of leakage and, in some cases, provides a much more economical disposable underwear design. For example, because the undergarment lies flat against a wearer's body in at least the three main areas (front section, rear section, and crotch section), the undergarment is about to provide a smooth contoured fit to the body, such that any gaps caused by overlapping materials are reduced or eliminated. By reducing or eliminating gaps between the garment and the body, the undergarment of the present disclosure provides improved leak resistance over prior art constructions. Additionally, the elastomeric composite provides consistent pressure and smooth contact against the leg and waist during wear when it is stretched, such that improved performance against leakage is obtained.

The smooth interface of the undergarment with the body provides improved comfort for the wearer and reduces the risk of skin irritation, particularly around the crotch and waist areas of the consumer, which are some of the most sensitive areas of the body. More specifically, the elastomeric composite design of the present disclosure eliminates the need for individual elastic strands (under high tension) and stiff materials (nonwoven & adhesive) along the leg openings, which are commonly found in current disposable underwear designs. In addition, the elastomeric composite design of the present disclosure allows for a wearer to participate in physical activities that may otherwise cause irritation, such as active motion of the wearer during walking or running exercises, which generally increases the rubbing action of material against the skin. The softer material and lower tension elastic provided by the undergarment of the present disclosure reduces the risk of skin irritation long the leg and crotch area of the consumer.

Furthermore, by providing different stretching characteristics for each given section, material elasticity and gasketing is increased, especially around the circumference of the leg openings, where leakage is more likely. Improvement in elasticity is due to both the type of elastomeric materials used and the way they are strategically positioned within the product. The front and back chassis of the product are designed to stretch in the machine direction (MD), which elongate in the cross-section (horizontally) along the waist, hip and thighs. The crotch section of the product is designed to stretch in the cross direction (CD), which elongate in the longitudinal direction (vertically) along the legs and crotch area. The combination of these three separate elastomeric composite sections and the manner in which they are orientated in the product, maximizes the amount of total elastic elongation. This theory has been verified in product stretch testing, as illustrated in Table 1 below:

TABLE 1

Product Stretch Testing

| Product | Size | Maximum Leg Circumference | Difference |
|---|---|---|---|
| Prototype 1 | L/XL | 1038 millimeters | |
| Prototype 2 | L/XL | 1092 millimeters | +54 millimeters |
| Prototype 1 | S/M | 964 millimeters | |
| Prototype 2 | S/M | 1038 millimeters | +74 millimeters |

Testing of two prototypes was performed. Prototype 1 is an elastic composite F (with MD stretch) used in the front, back and crotch sections, while Prototype 2 is an elastic composite F (with MD stretch) in the front and rear sections and elastic composite H (with CD stretch) in the crotch section, which is consistent with the disposable underwear product chassis of the present disclosure.

For testing of both prototypes, the "minimum" leg circumference was the same for similar product sizes. As shown in the table above, the elastic elongation (expansion) increased by simply replacing the elastic composite F (with MD stretch) with an elastic composite H (with CD stretch)

for the crotch section. The increase was over two inches for L/XL size and nearly three inches for S/M size, using the same product dimensions.

Thus, the construction of the disposable underwear product chassis of the present disclosure allows for a decrease of the "minimum" dimension of leg circumference, while still being able to meet the original "maximum" dimension of leg circumference. By decreasing the "minimum" dimension of leg circumference, the overall elastic tension is increased and the possibility of open gaps is reduced. This improvement in "gasketing", along the leg openings, will help reduce the possibility of leakage and provide increased "sense of security" to the consumer. Consumer use testing has revealed that "tighter" leg openings in the product, with no gaps, will make most consumers feel more confident that the product will provide superior absorbency performance and will not leak. If the elastic tension will increase along the leg openings, one may think that it will increase red marking and irritation to the skin. However, in this new product concept, that will not be the case. The elastomeric composite materials (with both MD and CD Stretch), used along the leg openings, are constructed of soft elastic film and nonwovens. The "flat" elastic film spreads out the force (elastic tension) along a larger surface area, which is much different than elastic strands, which direct the force (elastic tension) to a single point that is much smaller in surface area. This can cause red marking and irritation to the skin, if the elastic tension is too tight. If the elastic tension is too loose, the product will leak. Thus, the right balance of elastic tension and spreading out the forces along a larger surface area is required to achieve both a comfortable and anti-leak gasket at the leg area.

Figure 2:
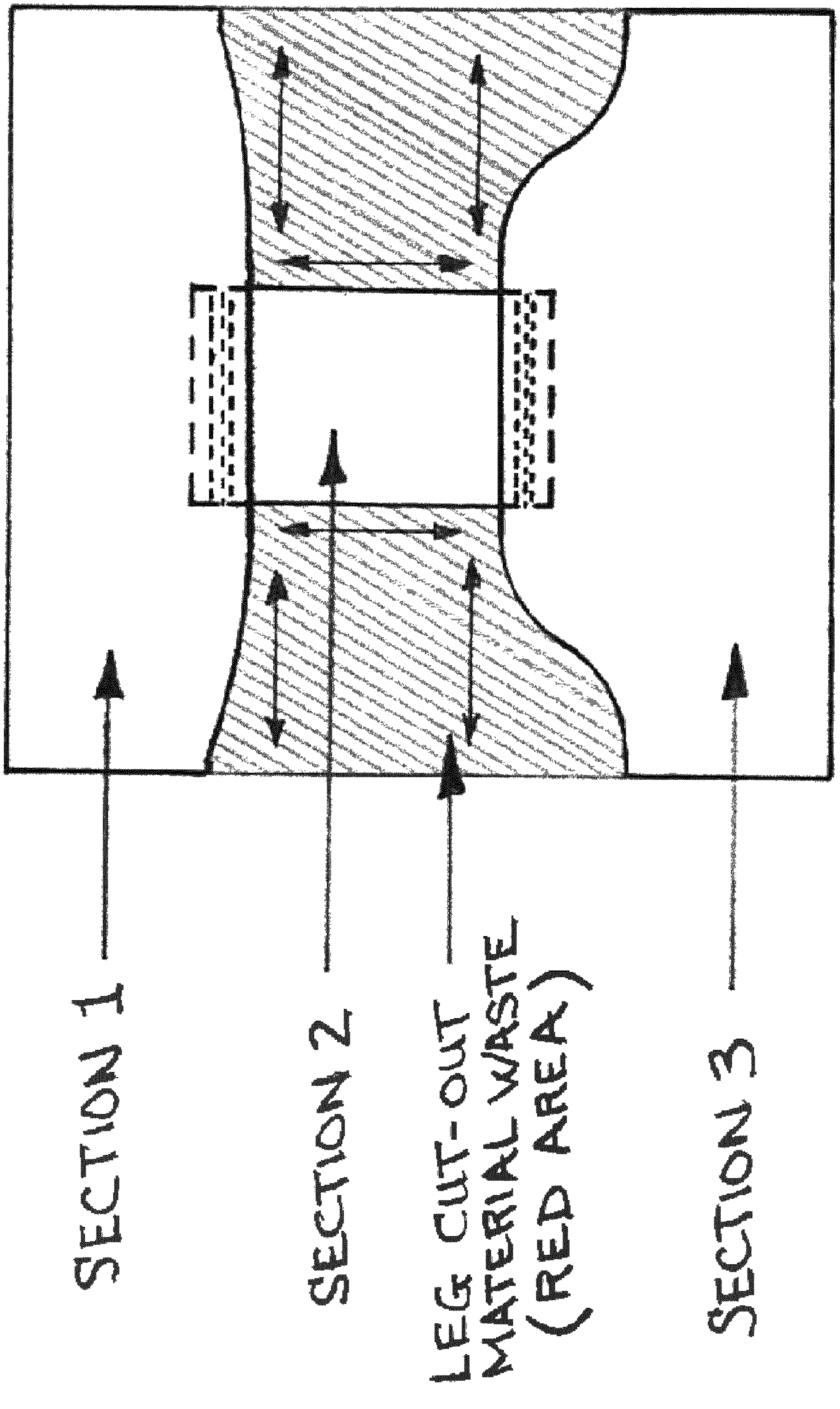
FIG. 2 is a top plan view of the disposable underwear of FIG. 1, illustrating what would constitute typical or normal material waste along leg cut-out sections (via conventional underwear design construction).
Figure 3:
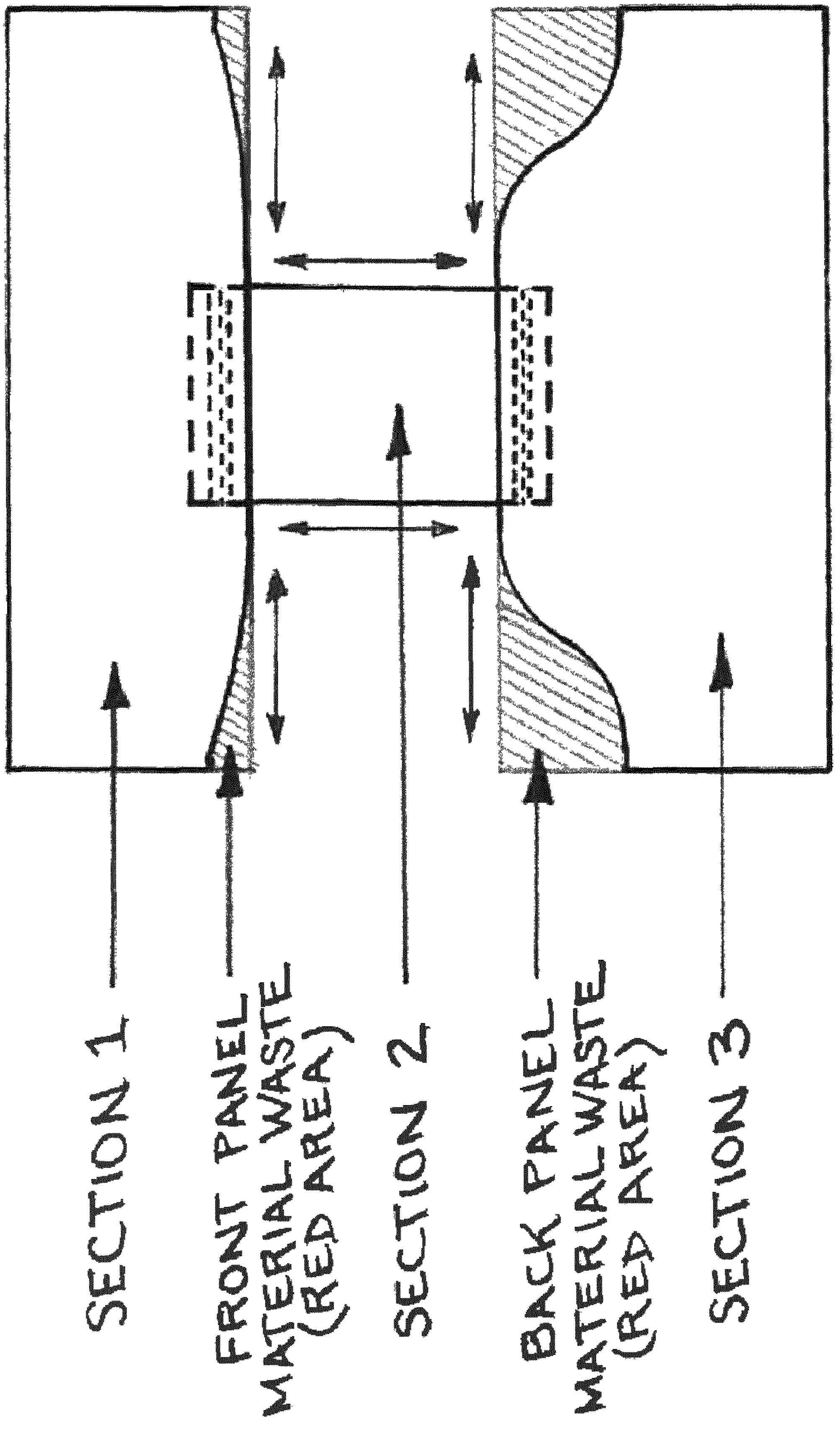
FIG. 3 is a top plan view of the disposable underwear of FIG. 1, illustrating reduced material waste along leg cut-out sections.
Figure 5:
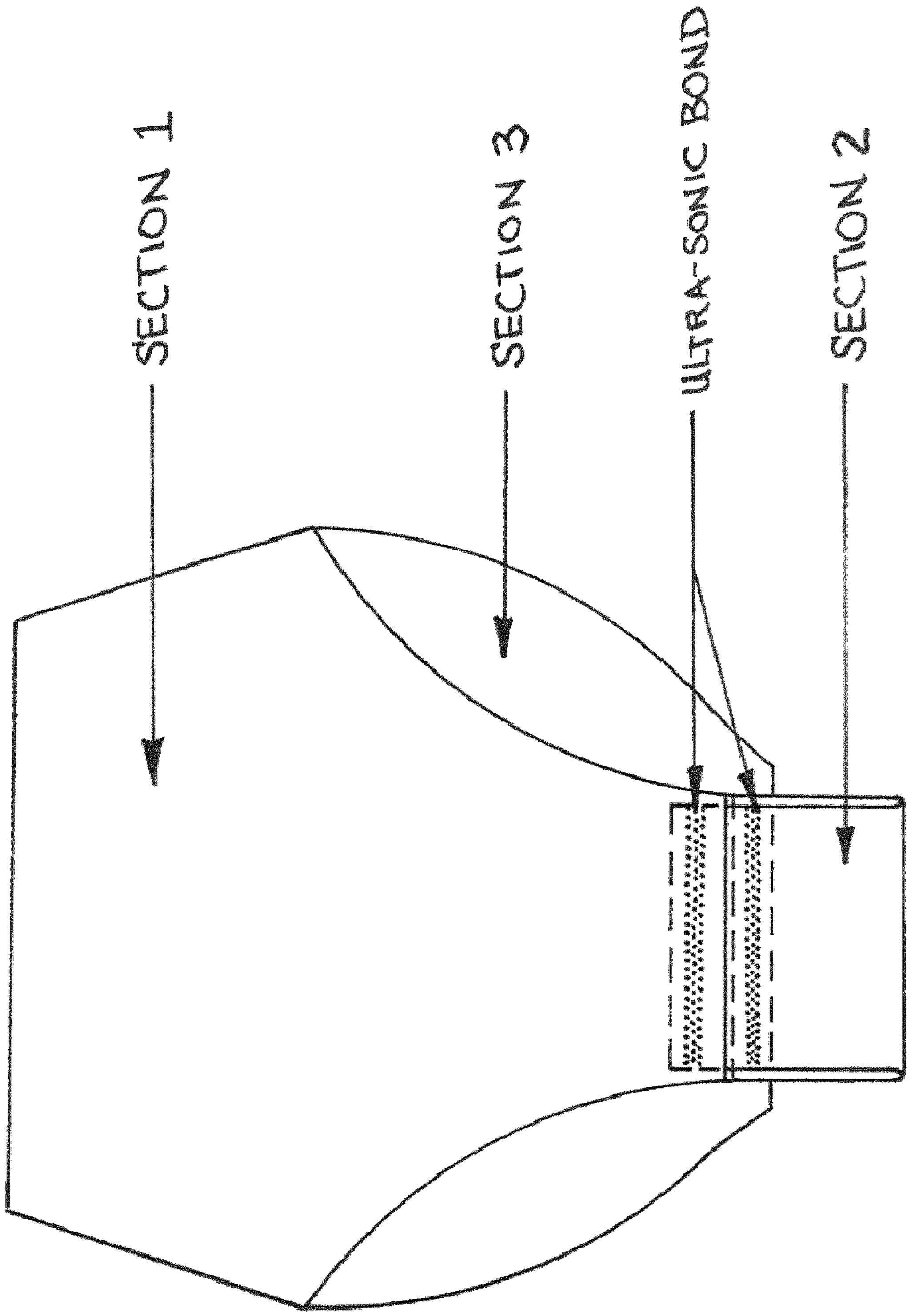
FIG. 5 is a front view of another embodiment of disposable underwear consistent with the present disclosure, illustrating the underwear in a folded and sealed state and having an anatomically-shaped design.
Figure 6:
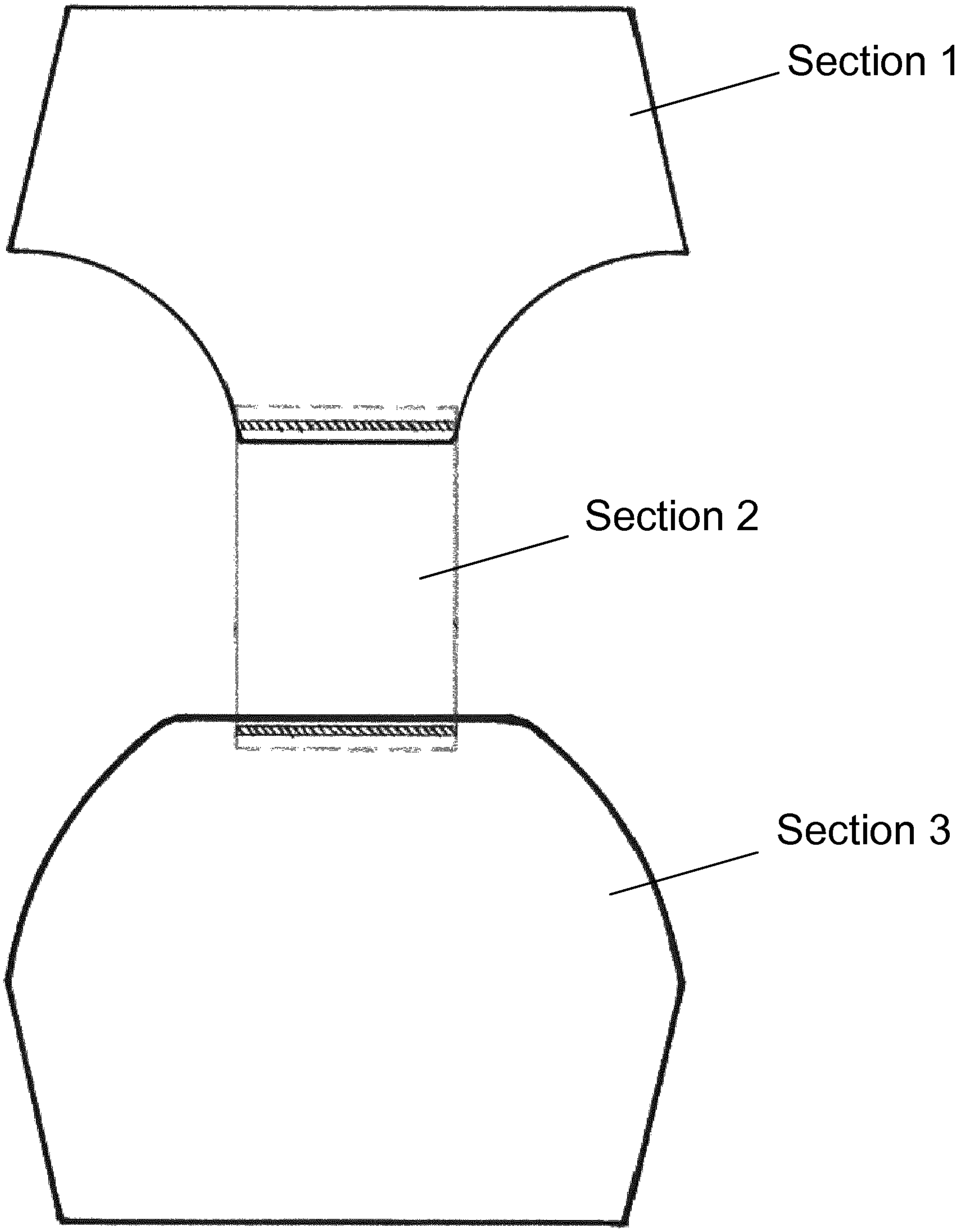
FIG. 6 is a top plan view of the disposable underwear of FIG. 5 in an unfolded and unsealed state, illustrating reduced material waste along leg cut-out sections.
Figure 7:
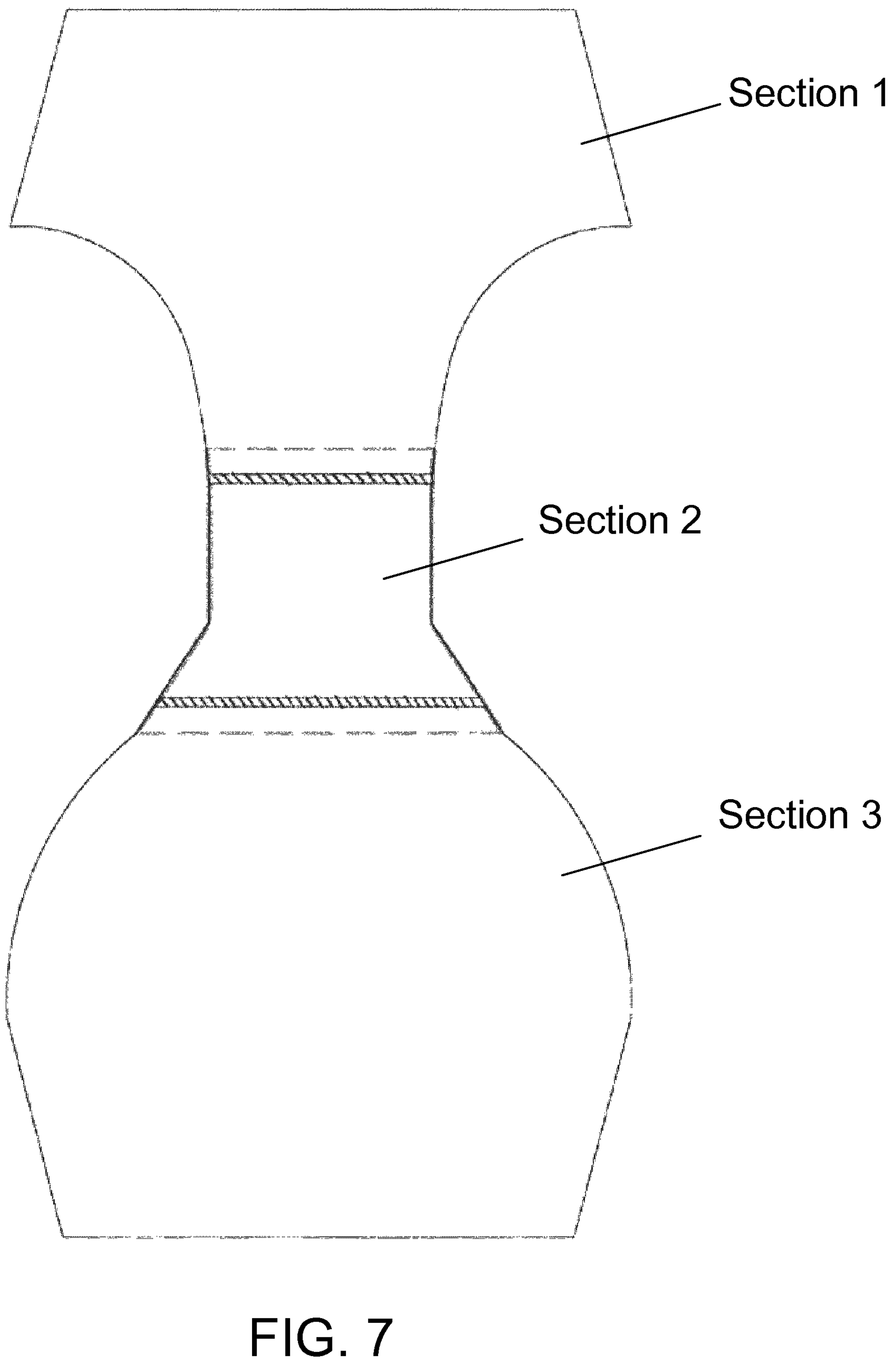
FIG. 7 is a top plan view of the disposable underwear of FIG. 5 in an unfolded and unsealed state, illustrating what would constitute typical or normal material waste along leg cut-out sections (via conventional underwear design construction).
Figure 8:
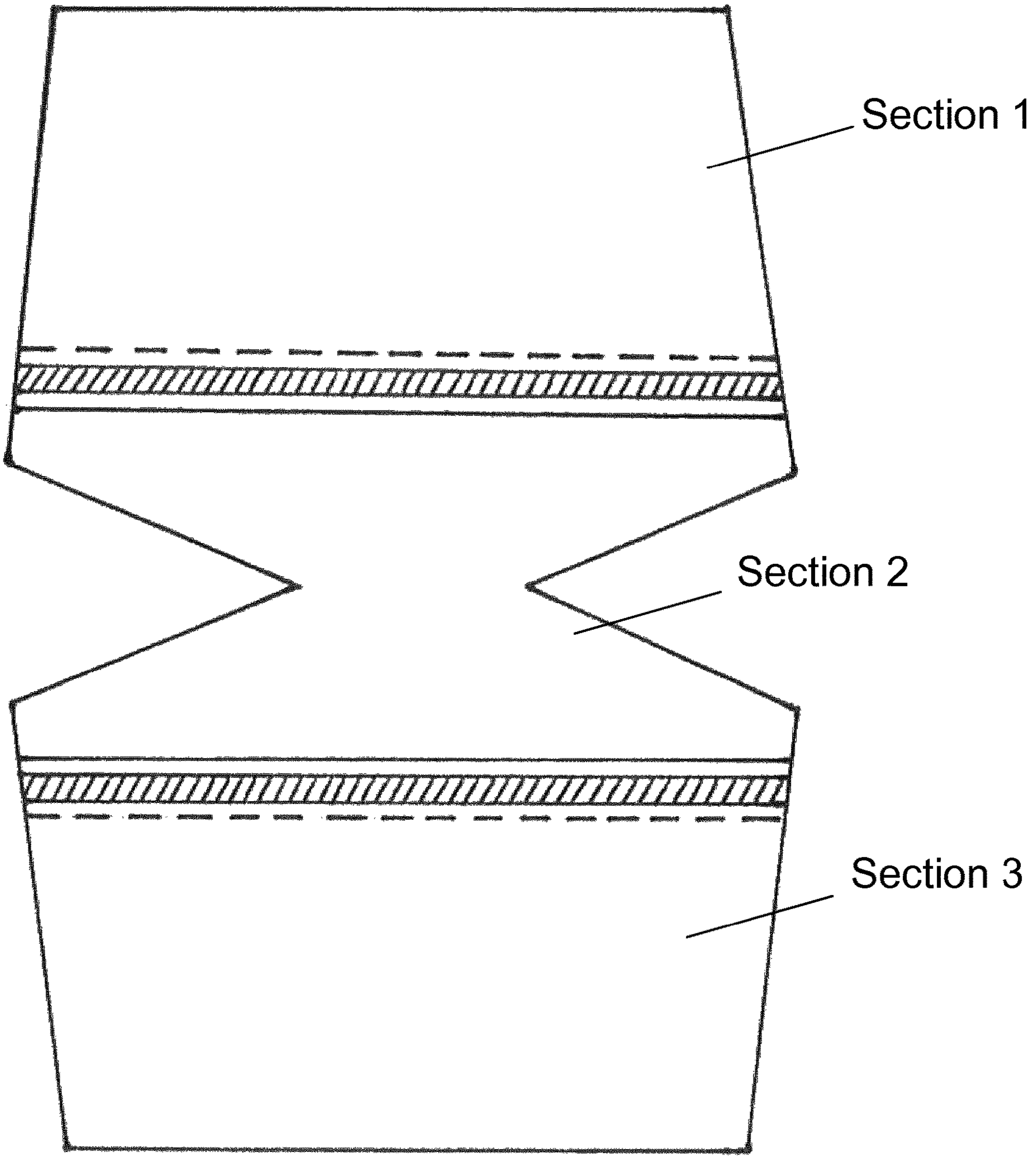
FIG. 8 is a top plan view of another embodiment of disposable underwear consistent with the present disclosure, illustrating the underwear in an unfolded and unsealed state and having a boxer short shape.

The use of at least three separately constructed sections (i.e., the front, rear, and crotch section, which are then coupled to one another to form the final undergarment product (via ultrasonic bonding or the like) minimizes the amount of waste of what could otherwise be an expensive elastomeric material. In particular, less material is necessarily required to be removed during the manufacturing process, as compared to the amount of material required to be removed if the undergarment was made entirely from single sheets of elastomeric composites. FIG. 2 is a top plan view of the disposable underwear of FIG. 1, illustrating what would constitute typical or normal material waste along leg cut-out sections (via conventional underwear design construction). FIG. 3 is a top plan view of the disposable underwear of FIG. 1, illustrating reduced material waste along leg cut-out sections. FIG. 5 is a front view of another embodiment of disposable underwear consistent with the present disclosure, illustrating the underwear in a folded and sealed state and having an anatomically-shaped design. FIG. 6 is a top plan view of the disposable underwear of FIG. 5 in an unfolded and unsealed state, illustrating reduced material waste along leg cut-out sections. FIG. 7 is a top plan view of the disposable underwear of FIG. 5 in an unfolded and unsealed state, illustrating what would constitute typical or normal material waste along leg cut-out sections (via conventional underwear design construction). FIG. 8 is a top plan view of another embodiment of disposable underwear consistent with the present disclosure, illustrating the underwear in an unfolded and unsealed state and having a boxer short shape.

As previously described, the disposable underwear consistent with the present disclosure may also contain an absorbent core for collecting bodily fluids or even excrement. For example, the disposable underwear may be used for menstrual and/or incontinence use. This would be more convenient for the consumer overall.

Figure 4:
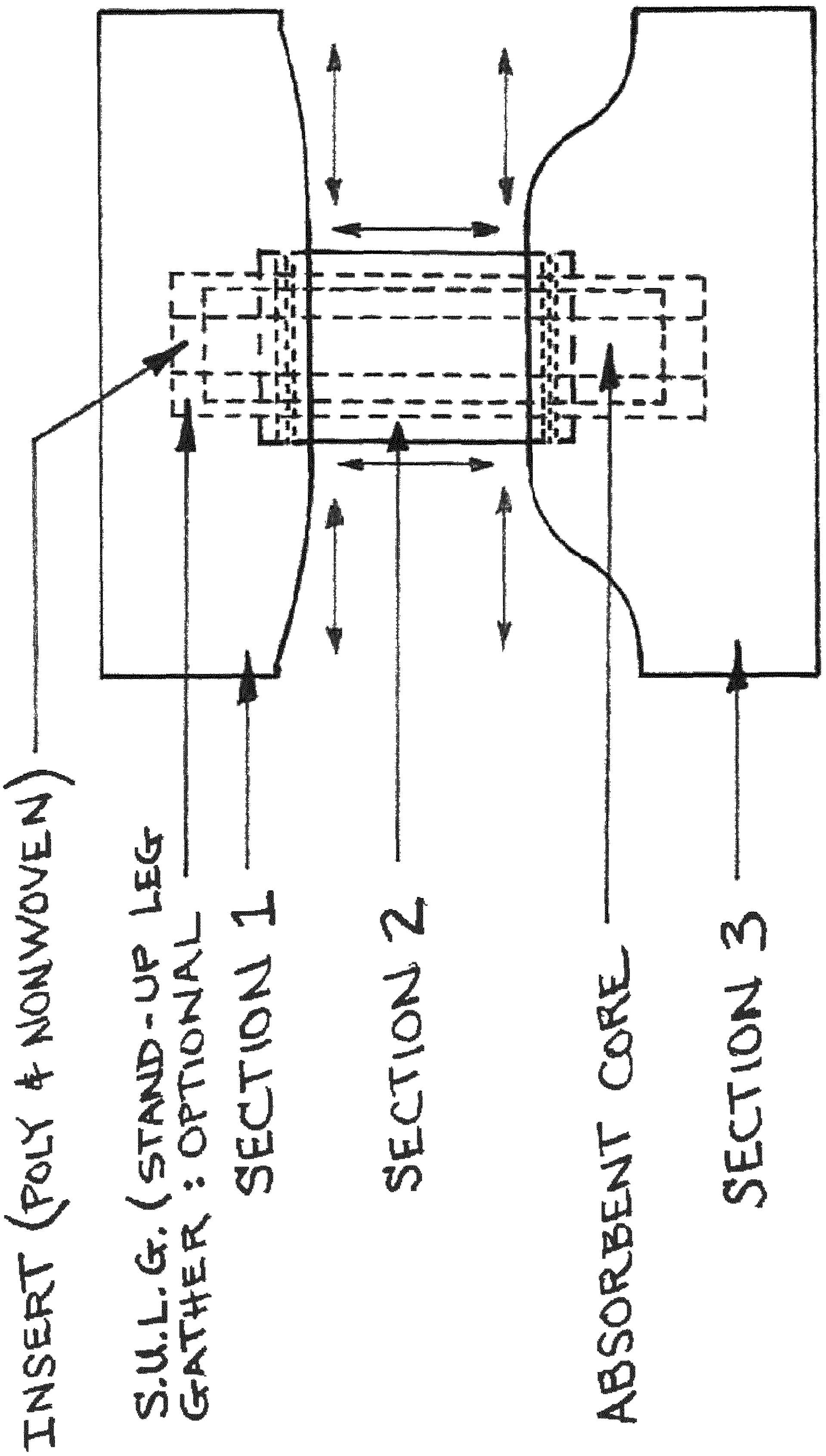
FIG. 4 is a top plan view of another embodiment of disposable underwear consistent with the present disclosure, illustrating the underwear including an absorbent core and insert provided within at least the crotch section, as well as a stand-up leg gather. The disposable underwear may be useful as a disposable incontinence product.

FIG. 4 is a top plan view of another embodiment of disposable underwear consistent with the present disclosure, illustrating the underwear including an absorbent core and insert provided within at least the crotch section, as well as a stand-up leg gather (SULP). The disposable underwear may be useful as a disposable incontinence product.

The absorbent core may generally include an absorbent material, a nonabsorbent material, and a combination thereof. For example, the absorbent core may include one or more of: "pulp only" core; "pulp & SAP" core; "pulp & SAP & tissue" core; "pulp & SAP nonwoven" core, "airlaid composite" core; "airlaid composite" core with cotton fibers; "rayon viscose" core; "rayon viscose & pulp" core; "rayon viscose & SAP" core; "rayon viscose & pulp & SAP" core; "rayon viscose & pulp & SAP & tissue" core; "tissue" core; "tissue & SAP" core; "creped tissue or paper towel" core; "creped tissue with SAP" core; "pulp & curly fiber" core; "pulp & curly fiber & SAP" core; SAP and nonwoven composite core (Pulpless); and "pulp & curly fiber & SAP & tissue" core.

The absorbent core may be comprised of multiple layers or structures. For example, as shown, the absorbent core may include at least three absorbent core structures. Optionally, more than three core structures can be used. Optionally, one or more core structures can be used, and the one or more core structures can have a variable thickness, or can have non-homogeneously-distributed constituent parts. For example, a unitary but non-homogenous core structure can have a portion that comprises fluff without SAP and another portion that comprises fluff with SAP, and optionally another portion that comprises fluff with a different proportion of SAP relative to fluff. The multicore design of the absorbent core is discussed in co-pending international application titled "Multi-Core Absorbent Article", having application no. PCT/US2016/012710, and filed Jan. 8, 2016, the content of which is incorporated by reference herein in its entirety.

In the case of an absorbent core for menstruation, it would mainly comprise of Pulp fibers to absorb blood and other high viscosity fluids & solids. One absorbent material that would be suitable is Golden Isles fluff pulp (Grades 4865 or 4875), which have exceptional absorbency rate, anti-bacterial properties and are capable of capturing & neutralizing malodors. They are available from Georgia Pacific located in Atlanta, GA. The pulp board would be ground into fluff fibers, formed in vacuum pockets and enwrapped between a soft Top Sheet made of SBPP (Spunbond Polypropylene) Nonwoven (hydrophilic) and a soft Back Sheet made of Poly Film (fluid-impervious/hydrophobic). The Poly Film may also be microporous and breathable, if so desired. One Top Sheet Nonwoven material that would be suitable is 12 gsm SBPP from Berry Global located in Charlotte, NC. One Poly Film material that would be suitable is 0.55 mil PE/PP (Polyethylene/Polypropylene) Blend Film available from Berry Global located in Chippewa Falls, WI. Construction Adhesive will be used to hold the absorbent core system together. One Construction Adhesive that would be suitable is F-5603 olefin available from H.B. Fuller Company located in Vadnais Heights, MN.

In addition to being comprised of Pulp, the absorbent cores may also contain a small amount of SAP (Super Absorbent Polymer). This has a dual purpose. It will provide "extra" absorbent capacity and allow the product to be used as a combo Menstrual & Incontinence Pad. One SAP material that would be suitable is Favor Max 2010 available from Evonik Industries located in Greensboro, NC.

The absorbent core may also comprise of an Airlaid material, instead of Pulp fibers & SAP particles blended & formed in a vacuum pocket, as described earlier. Airlaids contain Pulp & Binder fibers, which gives it improved integrity when wet & under stress. One Airlaid material that would be suitable is Airlaid VH-145.101 (145 gsm) or VH-160.116 (160 gsm), which do not contain Superabsorbent Polymer (SAP). However, Airlaid materials may contain some SAP, in addition to Pulp & Binder fibers for dual use products (menstrual & incontinence care). Another Airlaid material that would be suitable would be VH-180.135 (180 gsm), which contains SAP. They are all available from Glatfelter Falkenhagen GmbH located in Pritzwalk, Germany.

The "shape" of the absorbent core may be symmetrical or asymmetrical, rectangular, hourglass, dog bone, etc. Usually, "hourglass shaped" cores are desired, since they are more anatomically correct. However, "wrapped" absorbent cores (Pulp/SAP) or Airlaids are usually "rectangular" in shape, to reduce material waste. Although they may be "shaped" as well for improved fit. The absorbent core may be single layer, dual layer or even multiple layers depending on the use. Products used for overnight or require higher absorbent capacities, may use a dual core system, while products used for day or require lower absorbent capacities, may use a single core system. The single core system is usually thinner and lighter in weight.

SULG (Stand-Up Leg Gathers) or Cuffs may also be added to the product, if additional leakage performance is needed. They are mostly used in Incontinence care products, however they can be used for Feminine care products as well. The height of the SULG or Cuffs is usually higher in Incontinence care products vs. Feminine care products.

In the case of an absorbent core for incontinence, it would mainly comprise of a mixture of Pulp fibers and SAP (Super Absorbent Polymer) particles (blended together) to absorb high quantities of urine. Usually, the percentage of SAP vs. pulp is higher for incontinence care products versus menstrual care products due to the fact that SAP absorbs approximately four to five times the amount of pulp, in a gram (absorbent weight) per gram (fluid absorbed) basis.

As mentioned before, the absorbent core may be a single layer or have multiple layers depending on the absorbent capacity needed. For instance, "overnight" incontinence products may comprise of two or more layers, while "daytime" incontinence products may comprise of a single layer. If more than one absorbent layer is used, the core shape and size may be different as well. The Top Core may be mostly rectangular shaped (with round ends), while the Bottom Core may be hourglass shaped.

Also mentioned before, is the fact that the absorbent core may also comprise of an Airlaid material. In addition, the material may be a combination of Airlaid and ADL (Acquisition Distribution Layer) made of high-loft Nonwoven. One material combination that would be suitable is a Hybrid Airlaid VH-270.203 (270 gsm) available from Glatfelter Falkenhagen GmbH located in Pritzwalk, Germany. When using this material combination, it eliminates the need for an additional "cut & place" unit on the machine. Most machines already have a "cut & place" unit, along with an unwind station, to apply ADL (Acquisition Distribution Layer) on top of the absorbent core. One "preferred embodiment" of the absorbent core would comprise of a combined Airlaid and ADL material that is "cut & placed" on top of Pulp/SAP single core. This would provide a dual absorbent core system with ADL. The combined Airlaid and ADL material would be cut shorter in length and be narrower in width vs. Pulp/SAP single core. It would also be less likely to rope, bunch & crack, thus providing improved integrity when wet and under stress.

As mentioned before, SULG or Cuffs can be added to the new product to improve leakage performance. The SULG or Cuff will comprise of hydrophobic SMS (Spunbond/Meltblown/Spunbond) Nonwoven available from Berry Global located in Charlotte, NC. The basis weight would be around 13.5 gsm.

Figure 9:
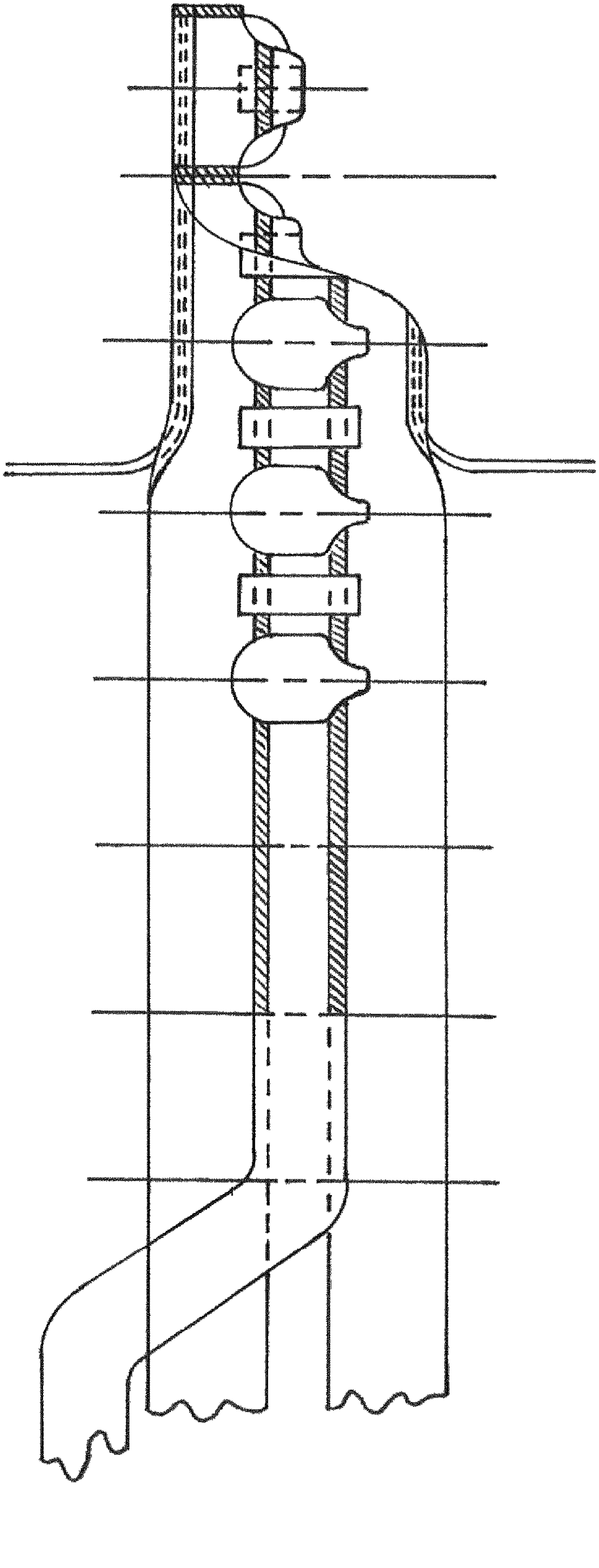
FIGS. 9 and 10 are schematic representations of a method for manufacturing a disposable underwear in accordance with the present disclosure.
Figure 10:
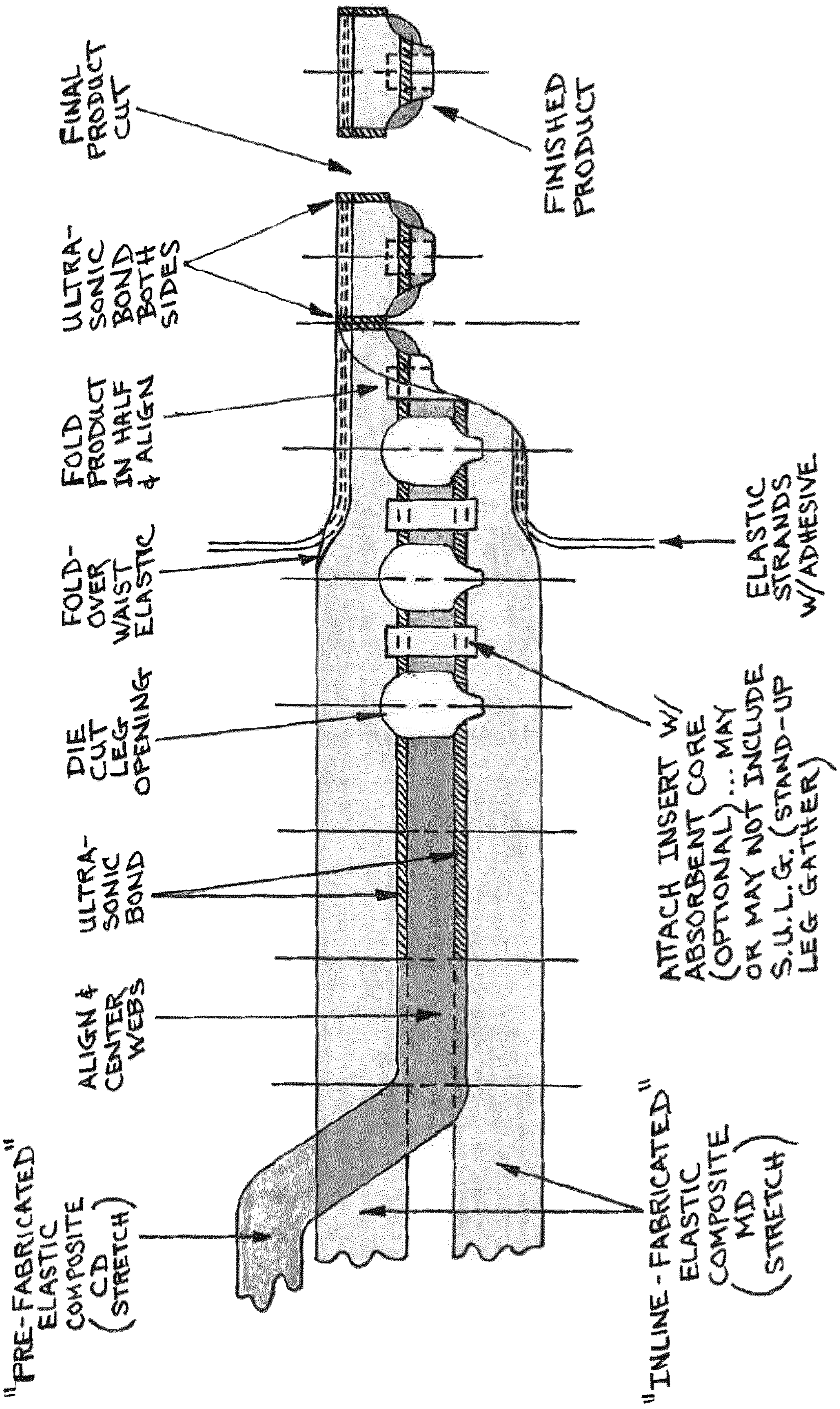

FIGS. 9 and 10 are schematic representations of a method for manufacturing a disposable underwear in accordance with the present disclosure. It should be noted that FIGS. 9 and 10 do not illustrate the manner in which the front and rear sections the Front and Rear sections of the product chassis are constructed and bonded on the machine. It is explained below, along with the rest of the manufacturing process. The steps for manufacturing a disposable underwear product chassis consistent with the present disclosure are as follows:

1. A soft nonwoven is unwound and slit in half on the machine. One nonwoven material that would be suitable is SMS (Spunbond/Meltblown/Spunbond) with Super CD Rod "embossing pattern" available from Fitesa located in Simpsonville, SC. One half of the material would be used on the "outside" of the Front Chassis and the other half on the "outside" of the Back Chassis.

2. Another nonwoven is unwound and slit in half on the machine. One nonwoven material that would be suitable is SMS (Spunbond/Meltblown/Spunbond) available from Berry Global located in Charlotte, NC. One half of the material would be used on the "inside" of the Front Chassis and the other half on the "inside" of the Back Chassis.

3. An elastic film would be unwound and slit in half on the machine. One elastic film that would be suitable is from 3M Corporation located in Minneapolis, MN. One half of the elastic material would be stretched, placed and aligned in between the nonwoven of #1 and #2 above and used in the Front Chassis. The other half of the elastic material would be stretched, placed and aligned in between the nonwoven of #1 and #2 above and used in the Back Chassis. The elongation of stretch would be around 200%-450% in the MD (Machine Direction).

4. The three plies of material (mentioned in #1, #2 and #3 above) would be ultrasonically bonded to each other and separated at specific dimension, creating an "open gap".

5. An elastic composite would be unwound and positioned within the "open gap" mentioned in #4 above, with a slight overlap on the Front and Rear sections of the product chassis. This material is unwound in the MD (Machine Direction) on the machine and stretches in the CD (Cross Direction). One elastic composite that would be suitable would be Hexaflex 15 available from Golden Phoenix Fiberwebs, Inc. located in Taipei, Taiwan.

6. The elastic composite (mentioned in #5 above) would be ultrasonically bonded to the Front and Rear sections of the product chassis.

7. The leg openings of the product chassis would be cutout with a rotary die cutter and the scrap removed & discarded.

8. Elastic strands would be unwound, stretched and adhered to the Front and Back edges of the product chassis. Then a portion of the Front and Back edges of the product chassis would be folded over the elastic strands. The folded material can be permanently bonded to the product chassis using a heat seal. One suitable elastic strand material would be 800 Decitex from Hyosung Corporation located in Seoul, South Korea.

9. The open product would be folded in half (creating the Front and Back portions) and ultrasonically sealed at the Left & Right sides of the chassis, to create an enclosed "pull-up" product.

10. The product would be cut as the final stage to create individual "disposable underwear" pieces ready to be folded, stacked and enwrapped in a package.

By providing different stretching characteristics for each given section, the product chassis provides a superior fitting undergarment with improved comfort, as well as reducing the risk of leakage and, in some cases, provides a much more economical disposable underwear design. For example, because the undergarment lies flat against a wearer's body in at least the three main areas (front section, rear section, and crotch section), the undergarment is about to provide a smooth contoured fit to the body, such that any gaps caused by overlapping materials are reduced or eliminated. By reducing or eliminating gaps between the garment and the body, the undergarment of the present disclosure provides improved leak resistance over prior art constructions. Additionally, the elastomeric composite provides consistent pressure and smooth contact against the leg and waist during wear when it is stretched, such that improved performance against leakage is obtained.

The smooth interface of the undergarment with the body provides improved comfort for the wearer and reduces the risk of skin irritation, particularly around the crotch and waist areas of the consumer, which are some of the most sensitive areas of the body. More specifically, the elastomeric composite design of the present disclosure eliminates the need for individual elastic strands (under high tension) and stiff materials (nonwoven & adhesive) along the leg openings, which are commonly found in current disposable underwear designs. In addition, the elastomeric composite design of the present disclosure allows for a wearer to participate in physical activities that may otherwise cause irritation, such as active motion of the wearer during walking or running exercises, which generally increases the rubbing action of material against the skin. The softer material and lower tension elastic provided by the undergarment of the present disclosure reduces the risk of skin irritation long the leg and crotch area of the consumer.

The use of at least three separately constructed sections (i.e., the front, rear, and crotch section, which are then coupled to one another to form the final undergarment product (via ultrasonic bonding or the like) minimizes waste of what could otherwise be an expensive elastomeric material. In particular, less material is necessarily required to be removed during the manufacturing process, as compared to the amount of material required to be removed if the undergarment was made entirely from single sheets of elastomeric composites.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof

The invention claimed is:

1. A method for making a disposable absorbent product comprising steps of:
- providing a front section material in a machine direction, said front section material comprising a front section elastomeric composite including an elastomeric material and configured to stretch in the machine direction upon application of a force thereto,
- providing a rear section material in the machine direction, said rear section material comprising a rear section elastomeric composite including an elastomeric material and configured to stretch in the machine direction upon application of a force thereto; and
- providing a crotch section material in the machine direction, between the front section material and the rear section material, said crotch section material comprising a crotch section elastomeric composite including an elastomeric material and configured to stretch in a cross direction substantially transverse to the machine direction upon application of a force thereto;
- coupling the front and rear section materials to the crotch section material;
- cutting the front and rear section materials in order to obtain a plurality of product chassis, each comprising a front section of the front section material, a rear section of the rear section material, and a crotch section of the crotch section material;
- whereby the rear section material is provided separately from the front section material;
- whereby the crotch section material has stretching characteristics that differ from stretching characteristics of the front and rear section material; and wherein the crotch section elastomeric composite is designed to stretch in the cross direction and not stretch in the machine direction.

2. The method of claim 1, further comprising folding the rear section material on the front section material or folding the front section material on the rear section material, wherein the folding is performed downstream of the coupling, and upstream or downstream of the cutting, as seen in the machine direction.

3. The method of claim 1, wherein the coupling is done by ultrasonic bonding and/or the method further comprising coupling side edges of the front section of each obtained product chassis to side edges of the rear section thereof, in order to form a garment.

4. The method of claim 1, further comprising cutting leg openings extending at least in the crotch section material, and optionally extending in the front and rear section materials; wherein said leg openings have edges that are not folded towards the longitudinal axis of the absorbent product.

5. The method of claim 1, further comprising cutting leg openings extending at least in the crotch section material, wherein the cutting of leg openings is done after the step of coupling and before the step of cutting of the front and rear section materials; and/or further comprising providing the crotch section material with an insert assembly such that it is positioned within at least a portion of the crotch section, the insert assembly comprising at least an absorbent core including a liquid-absorbing material.

6. The method of claim 1, wherein the front section and/or rear section and/or crotch section elastomeric composite comprises at least a first substrate layer and a second substrate layer, each of which comprises a nonwoven material, and a third layer comprising an elastomeric material positioned between the first and second substrate layers.

7. Product chassis obtained according to the method of claim 1.

8. Disposable garment obtained according to the method of claim 1.

9. A disposable garment comprising:

a product chassis comprising:

a front section comprising an elastomeric composite including an elastomeric material and configured to stretch in a first direction upon application of a force thereto, the front section configured to be fitted against a front, or anterior, portion of a wearer's body;

a rear section comprising an elastomeric composite including an elastomeric material and configured to stretch in the first direction upon application of a force thereto, the rear section configured to be fitted against a rear, or superior, portion of the wearer's body; and a crotch section coupled between the front and rear sections, the crotch section comprising an elastomeric composite including an elastomeric material and configured to stretch in a second direction substantially transverse to the first direction upon application of a force thereto, the crotch section configured to be fitted against a crotch region of the wearer's body;

wherein the first direction is a machine direction and the second direction is a cross direction;

wherein said front section, rear section and crotch section are separate elastomeric composite sections coupled to one another to form the product chassis having a front chassis with a front edge and a back chassis having a back edge; wherein the product chassis is configured to receive legs of the wearer via leg openings, wherein said leg openings are formed by leg cut-out sections in the elastomeric composite of the front section and in the elastomeric composite in the rear section; whereby the crotch section material has stretching characteristics that differ from stretching characteristics of the front and rear section material; wherein an article further comprises elastic strands at the front chassis and elastic strands at the back chassis; and wherein a portion of the front edge is folded over the elastic strands at the front chassis; wherein a portion of the back edge is folded over the elastic strands at the back chassis; and wherein an elastic film is arranged by stretching, placing and aligning the elastic film in between a first and second nonwoven used in the front chassis, and wherein an elastic film is arranged by stretching, placing and aligning the elastic film in between a first and a second nonwoven used in the back chassis; wherein elongation of stretch of the front chassis and the back chassis is around 200% to 450% in the machine direction.

10. The disposable garment of claim 9, wherein the elastomeric composite is configured to stretch in a direction transverse to the direction in which the elastomeric material is applied to form the elastomeric composite and/or wherein the elastomeric composite is prefabricated and/or wherein the elastomeric composite is prefabricated.

11. The disposable garment of claim 9, wherein the elastomeric composite of the front and rear sections are assembled and fabricated on a manufacturing line; wherein the garment is free of individual elastic strands along the leg openings.

12. The disposable garment of claim 9, wherein the elastomeric composite comprises at least a first substrate layer and a second substrate layer, each of which comprises a nonwoven material.

13. The disposable garment of claim 12, wherein the elastomeric composite comprises a third layer comprising an elastomeric film positioned between the first and second substrate layers.

14. The disposable garment of claim 13, wherein the first and second substrate layers are coupled together by way of a seal, wherein the first and second substrate layers are sealed to one another via an ultrasonically bonded seal to thereby form a multilayered elastomeric composite.

15. The disposable garment of claim 9, wherein the elastomeric material is disposed between two substrate layers and wherein the elastomeric material is a stretchable adhesive adhering the two substrate layers together.

16. The disposable garment of claim 9, further comprising an insert assembly positioned within at least a portion of the crotch section, the insert assembly comprising at least an absorbent core including a liquid-absorbing material, wherein the insert assembly further comprises an acquisition layer disposed between the absorbent core and a first substrate layer.

17. The disposable garment of claim 9, wherein the product chassis is free of individual elastic strands along the leg openings.

18. A method for making a disposable absorbent product comprising steps of:

providing a front section material in a machine direction, said front section material comprising a front section elastomeric composite including an elastomeric material and configured to stretch in the machine direction upon application of a force thereto, providing a rear section material in the machine direction, said rear section material comprising a rear section elastomeric composite including an elastomeric material and configured to stretch in the machine direction upon application of a force thereto; and providing a crotch section material in the machine direction, between the front section material and the rear section material, said crotch section material comprising a crotch section elastomeric composite including an elastomeric material and configured to stretch in a cross direction substantially transverse to the machine direction upon application of a force thereto;

coupling the front and rear section materials to the crotch section material;

cutting the front and rear section materials in order to obtain a plurality of product chassis, each comprising a front section of the front section material, a rear section of the rear section material, and a crotch section of the crotch section material;

whereby the rear section material is provided separately from the front section material;

further comprising cutting leg openings extending at least in the crotch section material, further comprising providing the crotch section material with an insert assembly such that it is positioned within at least a portion of the crotch section, the insert assembly comprising at least an absorbent core including a liquid-absorbing material; and wherein the insert assembly has longitudinal side edges perpendicular to the machine direction and wherein the insert assembly is positioned such that said longitudinal side edges are located at a distance from the leg openings;

wherein the insert assembly is provided after the leg openings are cut.

19. The method of claim 18, wherein the leg openings are cut such that the leg openings are extending at least in the crotch section material and extending in the front and rear section materials.

20. The disposable garment of claim 9, further comprising an insert assembly that is positioned within at least a portion of the crotch section, the insert assembly comprising at least an absorbent core including a liquid-absorbing material;

wherein said leg openings are further formed by leg cut-out sections in the elastomeric composite of the crotch section and wherein said insert assembly is disposed at a distance from said leg cut-out sections in the elastomeric composite of the crotch section such that a portion of elastomeric composite is present between the insert assembly and the leg cut-out sections for an improved consistent seal with a leg of a wearer.

* * * * *